United States Patent [19]

Schock

[11] Patent Number: 5,088,485
[45] Date of Patent: Feb. 18, 1992

[54] RESPIRATION MASK

[76] Inventor: Peter B. Schock, 13109 NE. 33rd St., Bellevue, Wash. 98005

[21] Appl. No.: 532,276

[22] Filed: Jun. 1, 1990

[51] Int. Cl.$^5$ .............................................. A61M 16/00
[52] U.S. Cl. ........................... 128/202.28; 128/203.11; 128/205.25; 128/206.21; 128/206.29
[58] Field of Search ................. 128/205.25, 205.21, 128/206.26, 206.28, 207.12, 202.28, 203.11, 206.29

[56] References Cited

U.S. PATENT DOCUMENTS

| | | | |
|---|---|---|---|
| 2,990,838 | 7/1961 | Cross . | |
| 2,995,131 | 8/1961 | Elam et al. . | |
| 3,626,936 | 12/1971 | Barker | 128/203.11 |
| 3,802,428 | 4/1974 | Sherman . | |
| 4,050,457 | 9/1977 | Davidson . | |
| 4,510,931 | 4/1985 | Henderson et al. | 128/202.28 |
| 4,559,940 | 12/1985 | McGinnis | 128/202.26 |
| 4,697,587 | 10/1987 | Marinkovich | 128/203.11 |
| 4,711,237 | 12/1987 | Kaiser | 128/202.28 |
| 4,811,730 | 3/1989 | Milano | 128/203.11 |
| 4,819,627 | 4/1989 | Connors | 128/203.11 |
| 4,819,628 | 4/1989 | Eisenberg et al. | 128/203.11 |
| 4,827,923 | 5/1989 | Bishop et al. | 128/206.11 |
| 4,834,085 | 5/1989 | Webster, II | 128/203.11 |
| 4,858,605 | 8/1989 | Levy | 128/203.11 |
| 4,872,465 | 10/1989 | Kuntz et al. | 128/857 |
| 4,881,540 | 11/1989 | Vigilia | 128/202.28 |
| 4,909,245 | 3/1990 | Wollenhaupt | 128/203.11 |

FOREIGN PATENT DOCUMENTS

WO90/00910 2/1990 .................................................. 205.25/
2742213 3/1979 Fed. Rep. of Germany ....... 203.11/

*Primary Examiner*—Edgar S. Burr
*Assistant Examiner*—Eric Raciti
*Attorney, Agent, or Firm*—Christensen, O'Connor, Johnson & Kindness

[57] ABSTRACT

A respiration mask (10) including a shield (12) and a valve (14). The valve preferably includes two unidirectional elements (20) and (22) that allow air to flow therethrough, while limiting the reverse flow of contaminants. In use, the mask (10) is placed over a victim's face, with the shield covering the victim's face and the valve in the victim's mouth. A rescuer than performs mouth-to-mouth respiration in the standard fashion, with the shield and valve protecting the rescuer from victim contaminants.

19 Claims, 3 Drawing Sheets

RESPIRATION MASK

FIELD OF THE INVENTION

This invention relates generally to protective equipment and, more particularly, to protective equipment for use in the administration of medical treatment.

BACKGROUND OF THE INVENTION

Artificial respiration (AR) and cardiopulmonary resuscitation (CPR) are two widely taught and employed first aid procedures. AR is used to treat a victim who is no longer breathing and requires the victim's lungs to be periodically filled with air by some artificial means. This procedure ensures the continued oxygenation of the blood supplies to the various portions of the victim's body, until normal breathing can be restored.

CPR is used to treat a victim who is not breathing and whose heart has also stopped. In addition to the periodic filling of the lungs, CPR requires mechanical pressure to be periodically applied to the victim's chest to physically induce contractions of the heart and thereby maintain blood flow through the victim's cardiovascular system. The periodic filling of the victim's lungs with air, common to both AR and CPR, is collectively referred to herein as "respiration."

Although mechanical respirators have been developed for use in performing respiration, in many emergency situations, a mechanical respirator is simply not available. In such situations, a form of respiration known as "mouth-to-mouth" respiration is frequently used.

To perform mouth-to-mouth respiration, the person administering the first aid (the rescuer) first clears the victim's mouth of obstructions and tilts the victim's head back. Then, after pinching the victim's nose shut, the rescuer places his or her mouth over the victim's mouth and exhales to fill the victim's lungs with air. This last step is repeated periodically until the victim's natural breathing is restored or the treatment is otherwise to be discontinued.

As will be appreciated, mouth-to-mouth respiration potentially exposes the rescuer to various types of contamination from the victim. For example, the rescuer may be exposed to contamination from the victim's body fluids. In addition to the victim's saliva, the rescuer of a victim of traumatic or atraumatic cardiopulmonary arrest may be exposed to the victim's sweat, blood, and emesis, which are natural consequences of such arrests. Mouth-to-mouth respiration may also expose the rescuer to viral contamination from the victim. Included in such viral contaminants are hepatitis A, B, and C; human immunodeficiency virus (HIV), herpes simplex, and mononucleosis. The rescuer may further be exposed to fungal contaminants including tuberculosis, coccidiomycosis, and valley fever. Finally, mouth-to-mouth respiration may expose the rescuer to bacterial contaminants including pneumonia, staphylococcus, and streptococcus.

As can be expected, these potential forms of contamination may inhibit a rescuer from offering assistance. This is particularly true when, for example, the victim is unknown to the rescuer, as is usually the case when the rescuer is a member of a police or fire department or hospital staff. Even if assistance is provided, the evaluation of the potential risks to the rescuer may result in treatment being delayed.

As will be appreciated from the preceding remarks, it would be desirable to provide a way to reduce the risks associated with mouth-to-mouth resuscitation. In addition to providing protection against contaminants, the flow of air from the rescuer to the victim must not be impeded. Further, because mouth-to-mouth resuscitation is typically performed in emergency circumstances that cannot be anticipated, the device must be compact so that it can be easily and universally carried by emergency personnel, as well as members of the public, at all times. The device must also be low in cost if it is to be universally carried. Finally, the device must be simple to use so that it can be properly employed during emergency circumstances.

In conclusion, it would be desirable to provide a low-cost, compact, simple-to-use respiration mask that protects a rescuer from contaminants without impeding the flow of air to the victim.

SUMMARY OF THE INVENTION

In accordance with this invention, a mask is disclosed comprising a shield having a first side and a second side. The shield is for limiting the passage of fluid between the first side and the second side. A passage, coupled to the shield, allows air to pass from the first side to the second side of the shield, while limiting the passage of fluids from the second side to the first side of the shield.

As one example, the shield may be a flexible sheet having a rescuer side and a victim side. The passage may include a two-element unidirectional valve, coupled to the flexible sheet and projecting from the victim side. The unidirectional valve allows air to pass from the rescuer to the victim, yet limits the migration of contaminants from the victim to the rescuer.

BRIEF DESCRIPTION OF THE DRAWINGS

The invention will presently be described in greater detail, by way of example, with reference to the accompanying drawings, wherein.

DETAILED DESCRIPTION OF THE PREFERRED EMBODIMENT

Figure 1:
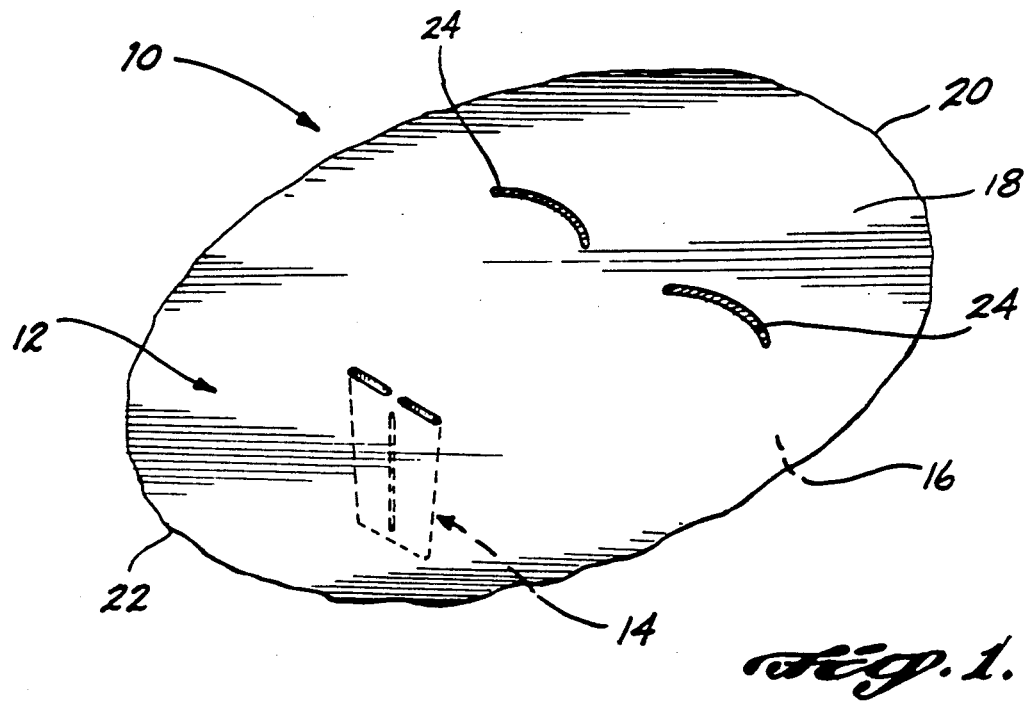
FIG. 1 is an illustration of a respiration mask constructed in accordance with this invention.

Referring now to FIG. 1, a mask 10 is illustrated for use in protecting a rescuer from victim contaminants during mouth-to-mouth respiration. The two main components of mask 10 are a shield 12 and valve 14. The shield 12 is designed to substantially cover the victim's face, and provide a general barrier between the victim and the rescuer. The valve 14 is designed to project into the victim's mouth and has a unidirectional, or one-way, construction that allows the rescuer to exhale through the valve, while obstructing the flow of contaminants from the victim to the rescuer.

The resultant mask 10 protects the rescuer, yet allows air to be smoothly passed to the victim. The mask 10 of FIG. 1 is further inexpensive, compact, simple to use, and disposable, ensuring its widespread use.

Addressing the components of mask 10 in greater detail, as noted above, the shield 12 is designed to substantially cover the face of the victim and provide a barrier between the rescuer and victim. As a result, contaminants present on the victim's face, including sweat, blood, emesis, and secretions, are confined to the victim, protecting the rescuer.

In the preferred embodiment, the shield 12 is simply an oval sheet of material having a "victim" side 16 and "rescuer" side 18. The oval sheet has a major diameter of roughly thirty centimeters, defined between the top 20 and bottom 22 of the mask 10, and a minor diameter of roughly twenty-five centimeters. A shield 12 having these dimensions should be large enough to provide the desired coverage of nearly all victims' faces. The oval sheet also has a thickness of roughly 2.5 millimeters. This thickness has been found suitable for ensuring that the shield 12 can be folded into a compact package, while remaining relatively resistant to accidental damage.

The shield 12 is preferably made of nonopaque or semitransparent latex. The latex is impermeable to most contaminants including, for example, sweat, blood, saliva, and emesis. Because the shield 12 is nonopaque, the rescuer can maintain visual contact with the victim's face, making it easier for the rescuer to provide the desired relative alignment between the shield 12 and the victim's face, as well as allowing the rescuer to more readily sense changes in the victim's condition.

The shield 12 also includes a pair of indication marks 24, spaced roughly ten centimeters from the top of the shield 12. The marks 24 are located symmetrically about the major axis of shield 12 and are preferably curved to roughly represent the victim's eyebrows. By aligning these "eyebrow" marks 20 with the victim's eyebrows, the desired orientation of the mask 10 on the victim's face is easily achieved by the rescuer.

Addressing now the valve 14, valve 14 projects from the victim side 16 of shield 12. Valve 14 is located on the major axis of shield 12 at a point roughly ten centimeters from the bottom 22 of mask 10. As noted above and described in greater detail below, valve 14 has a unidirectional construction that allows the rescuer to blow air through valve 14, while preventing the migration of contaminants from the victim to the rescuer.

Figure 2:
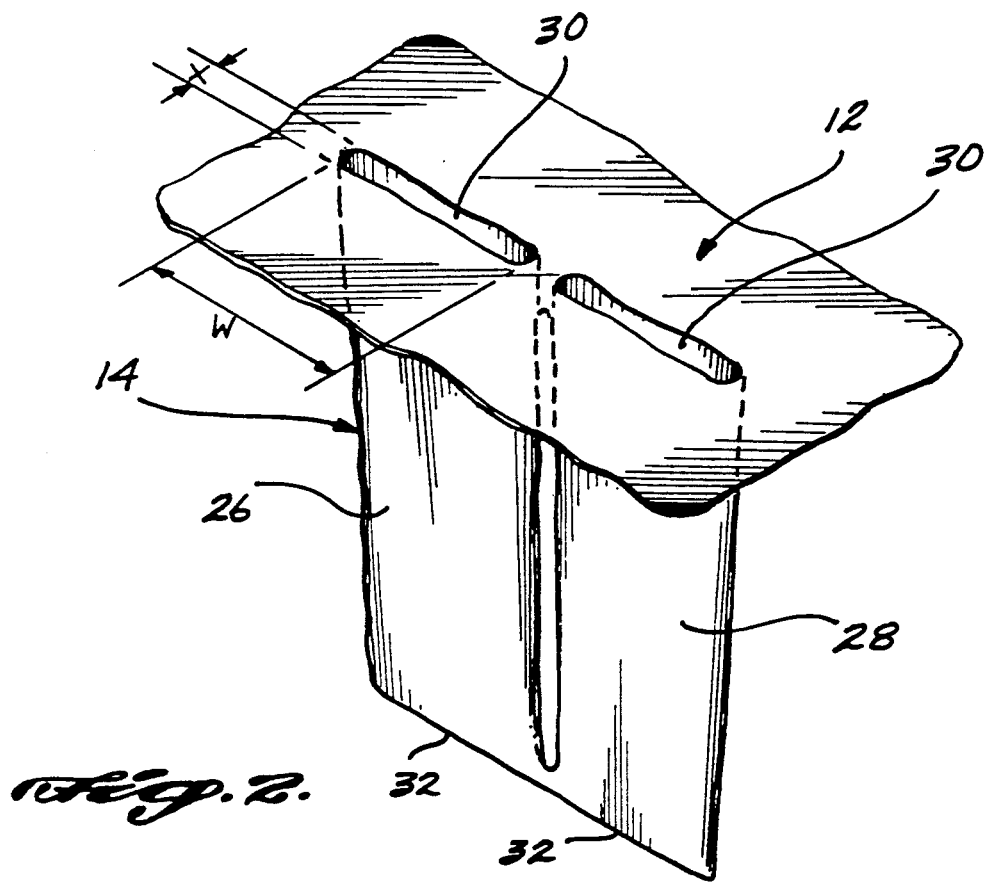
FIG. 2 is a detailed view of a valve portion of the respiration mask shown in FIG. 1.

Reviewing the construction of valve 14 in greater detail, the valve 14 is preferably made of the same latex material as shield 12. As shown in FIG. 2, valve 14 includes two parallel tubular elements 26 and 28 each having a "duckbill"-type unidirectional construction. Each element 26 and 28 is roughly four centimeters long and has an inlet end 30, coupled to shield 12, and an outlet end 32. The two elements 26 and 28 are spaced apart throughout their length, with the two outlet ends 32 being coupled together.

The elements 26 and 28 have a tapered construction, with the width w and thickness t of each element 26 and 28 generally decreasing from the inlet end 30 to the outlet end 32. More particularly, the width w of each element 26 and 28 is roughly one and one-half centimeters at inlet end 30 and one centimeter at outlet end 32. As will be appreciated from the cross-sectional view of FIG. 3A, the thickness t of each element 26 and 28 is constricted near both the inlet end 30 and outlet end 32, providing a double restriction against the passage of contaminants from the victim to the rescuer.

The basic mask 10 described above is used in the following manner. The indication marks 24 on shield 12 are used to establish the desired orientation of mask 10 with respect to the victim. The mask 10 is then placed over the victim's face. Because it is flexible, shield 12 conforms roughly to the victim's face and its nonopaque nature allows the rescuer to visually monitor the victim's condition.

Figure 4:
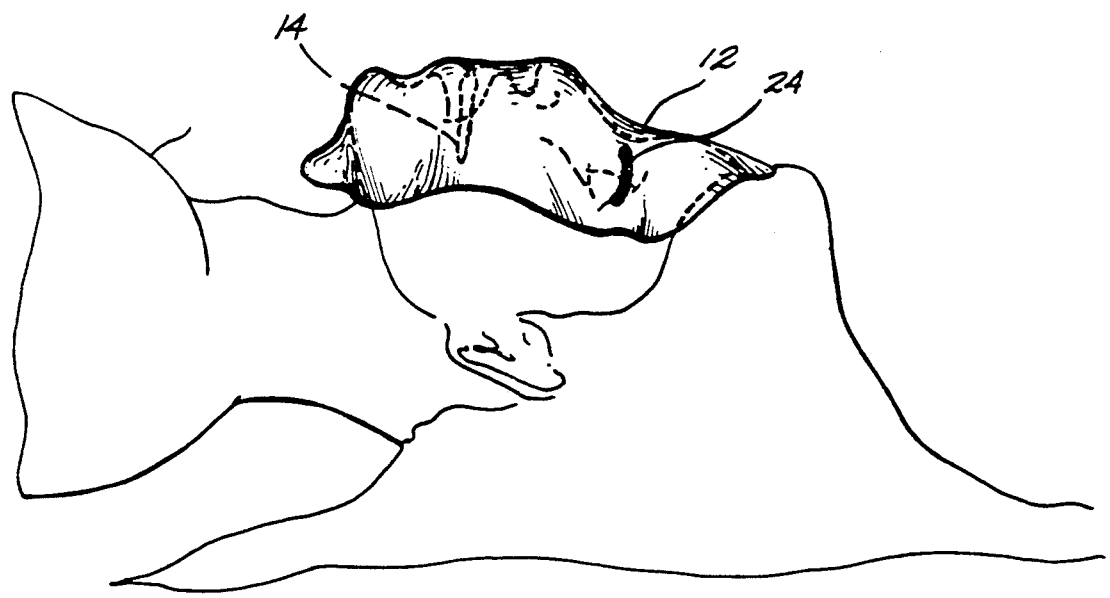
FIG. 4 is an illustration of the respiration mask of FIG. 1 positioned on the face of a victim to be respirated.

With shield 12 properly positioned, the valve 14 projects into the victim's mouth, as shown in FIG. 4. The valve elements 26 and 28 are long enough to ensure that the outlet end 32 of each element 26 and 28 provides air directly to the victim's throat during artificial respiration, enhancing the efficiency of the respiration being performed. Valve elements 26 and 28 cannot, however, be so long as to obstruct the victim's air passageways or cause the victim to gag.

Once the mask 10 is suitably placed on the victim's face, AR or CPR is performed in the normal manner, except that the shield 12 now provides a seal and barrier between the mouths of the rescuer and victim. Before the rescuer exhales, the individual elements 26 and 28 are in a closed position illustrated in FIG. 3A. As will be appreciated, in this position, the valve 14 blocks the flow of fluid, viral, fungal, and bacterial contaminants from the victim to the rescuer. Thus, the length of valve 14 also contributes to the protection provided. Even if the valve 14 did not completely seal shut, contaminants must still migrate the entire length of the valve 14 to reach the rescuer.

Figures 3A, 3B:
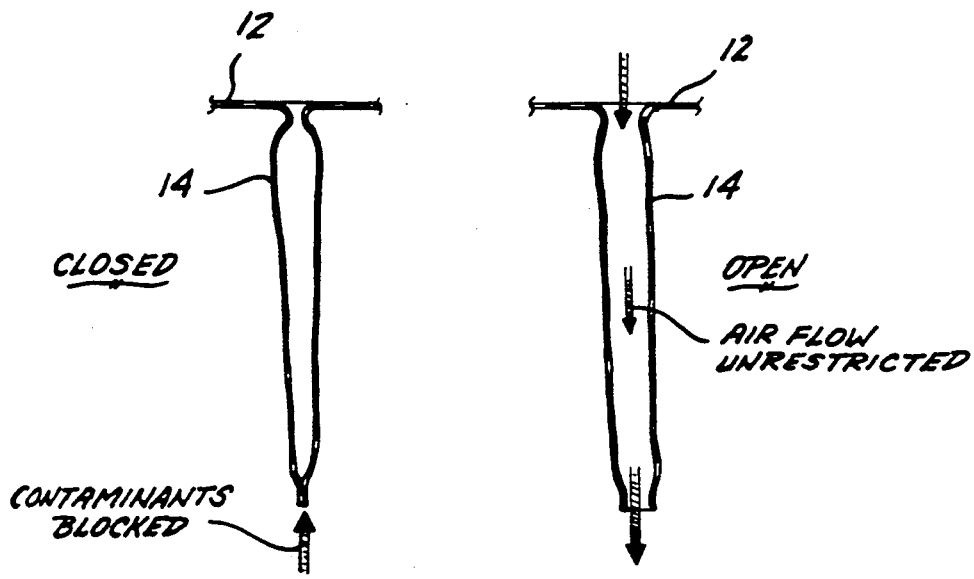
FIGS. 3a and 3b are sectional views of the valve of FIG. 2, illustrating the valve in closed and open positions.

When the rescuer exhales, the individual elements 26 and 28 of valve 14 are expanded to an open position, as shown in FIG. 3B, and maintained in the open position by the air flowing therethrough. The elements 26 and 28 are constructed to ensure that their cross-sectional area in this open position is sufficient to allow adequate air to be received by the victim. Once the rescuer stops exhaling, the elements 26 and 28 collapse due to their own elasticity and the pressure in the victim's lungs. The air in the victim's lungs is then allowed to escape from under the mask 10 before the process is repeated.

The dual-element construction of valve 14 shown in FIG. 2 has been found to be particularly successful in blocking the passage of contaminants from the victim to the rescuer. In that regard, the overall cross-sectional area of the two elements 26 and 28 in the open position is large enough to ensure adequate respiration of the victim, as noted above. By dividing the respiration passage through valve 14 into parallel paths, however, each outlet 32 is smaller and seals more easily and securely.

Although the dual-element valve 14 illustrated in FIG. 2 is thus preferred, a single-element, unidirectional, duckbill-style valve 14 could also be employed in its place. In that regard, such a unidirectional, duckbill-style, single-element valve 14 would also be tapered in width and thickness and would generally have the same length as the dual-element valve discussed above. As will be appreciated, other valve constructions including more than two elements or having a different type of operating mechanism could be employed as desired.

As will be appreciated, a mask 10 of the type described above is extremely inexpensive. As a result, there should be no significant cost barrier to universal ownership of masks and the mask 10 can also be disposed of after use.

Figure 5A:
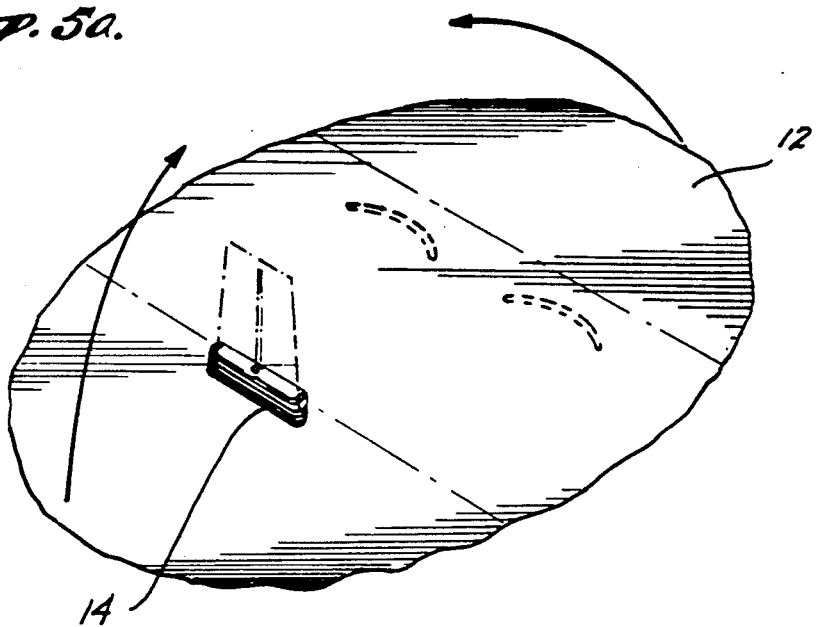
FIGS. 5a through 5d are illustrations of the steps involved in the packaging and unpackaging of the mask of FIG. 1.
Figure 5B:
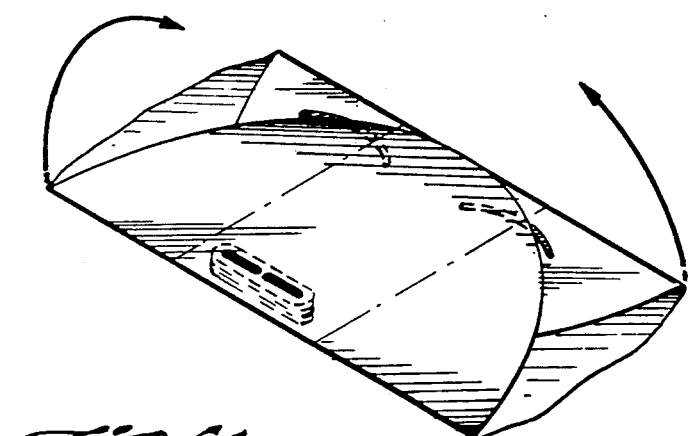
Figure 5D:
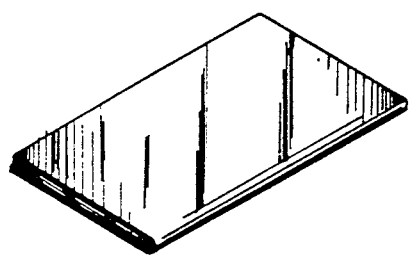
Figure 5C:
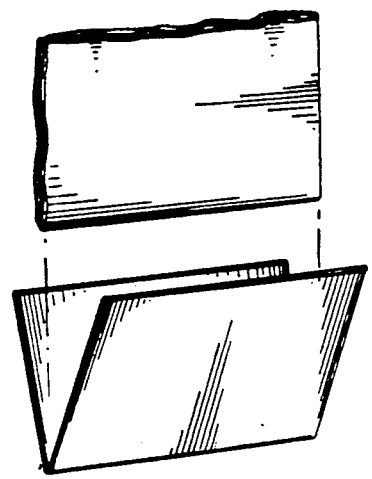

Given the flexible nature of the mask 10, mask 10 can also be conveniently stored for widespread carrying in anticipation of emergency situations. In that regard, the mask 10 is preferably packaged in the following manner, illustrated sequentially in FIG. 5. The flexible valve 14 is folded in a telescoping or accordian-like manner (see FIG. 5A) and the shield 12 is then folded about the valve 14 into a rectangle that is roughly 6.4 centimeters wide, 8.9 centimeters long, and 0.2 centimeter thick. (See FIGS. 5B and 5C.) The folded mask 10 is then received between the two halves of a folded card 34 (see FIG. 5D) and the entire package is either laminated or covered by a shrink wrap (see FIG. 5E). As will be appreciated, a package 36 having these dimensions can easily be carried in a wallet or purse, taking up no more space than a credit card.

When a mask 10 packaged in this manner is to be used, the mask 10 is first removed from the shrink wrap and card. Instructions for use of the mask 10, as well as general AR and CPR procedures, are provided on card. The shield 12 is then unfolded and positioned on the victim's face. The first time the rescuer exhales through valve 14, the air extends the folded or telescoped valve 14 into the victim's mouth to the desired position. The remaining steps in the use of mask 10 are then as described above.

Those skilled in the art will recognize that the embodiments of the invention disclosed herein are exemplary in nature and that various changes can be made therein without departing from the scope and the spirit of the invention. In this regard, and as was previously mentioned, the invention is readily embodied with either single- or dual-element valves. Further, it will be recognized that the thickness and construction of the shield may vary greatly. Because of the above and numerous other variations and modifications that will occur to those skilled in the art, the following claims should not be limited to the embodiments illustrated and discussed herein.

The embodiments of the invention in which an exclusive property or privilege is claimed are defined as follows:

1. A respiration face mask for use by a rescuer in administering at least artificial respiration to a victim, said mask comprising:
   protection means for substantially completely covering the victim's face to provide facial protection to the rescuer; and,
   a valve including first and second duckbill elements, each said duckbill element having an inlet end attached to said protection means and an outlet end, said outlet ends of said first and second duckbill elements being coupled to each other.

2. The mask of claim 1, wherein said protection means comprises a flexible sheet.

3. The mask of claim 2, wherein said flexible sheet has a roughly oval shape.

4. The mask of claim 3, wherein said flexible sheet is nonopaque.

5. The mask of claim 4, wherein said flexible sheet includes orientation marks for use in defining a desired orientation of said flexible sheet.

6. The mask of claim 1, wherein said first and second duckbill elements comprise relatively flat, tapered tubular elements.

7. The mask of claim 6, wherein said protection means is a sheet of flexible material and said first and second duckbill elements are also made of said flexible material.

8. A mask, for use by a rescuer in respirating a victim, comprising:
   a flexible sheet having a rescuer side and a victim side; and
   a valve including first and second tubular elements, each element having a proximal end coupled to said flexible sheet and a distal end, said first and second elements being coupled together at a point other than said proximal ends, said valve projecting from said victim side of said sheet and allowing air to pass from the rescuer to the victim while limiting the migration of contaminants from the victim to the rescuer.

9. The respiration mask of claim 8, wherein the flexible sheet has alignment means coupled to said sheet for allowing a desired relative orientation between said sheet and the face of the victim to be established.

10. The respiration mask of claim 9, wherein said alignment means comprises an indicator mark provided on said shield.

11. The respiration mask of claim 10, wherein said indicator mark comprises a pair of curved lines.

12. The respiration mask of claim 9, wherein said sheet is a flexible sheet of nonopaque latex material.

13. The mask of claim 12, wherein said valve is extendable into a victim's mouth.

14. The mask of claim 12, wherein said sheet comprises a foldable sheet.

15. The mask of claim 8, wherein said distal ends of said first and second elements are coupled together.

16. The mask of claim 8, wherein said first and second tubular elements comprise relatively flat, tapered duckbill elements.

17. The mask of claim 16, wherein said distal ends of said duckbill elements are constricted to limit the migration of contaminants from the victim to the rescuer.

18. The mask of claim 17, wherein said proximal ends of said duckbill elements are constricted to limit the migration of contaminants from the victim to the rescuer.

19. A method of protecting a rescuer during respiration of a victim comprising the steps of:
   providing a generally fluid-resistant barrier shield between the rescuer and victim; and
   providing a one-way passage for air to flow from the rescuer to the victim through a valve that includes first and second duckbill elements, each element having a proximal end and a distal end, said proximal ends of said first and second duckbill elements being coupled to said shield and said distal ends being joined together, said valve restricting the flow of fluid from the victim to the rescuer.

* * * * *